(12) United States Patent
Schleicher (10) Patent No.: US 8,709,030 B1
(45) Date of Patent: Apr. 29, 2014

(54) EXPLANTING IMPLANTABLE DEVICES

(75) Inventor: Brett Schleicher, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1493 days.

(21) Appl. No.: 12/322,137

(22) Filed: Jan. 28, 2009

Related U.S. Application Data (60) Provisional application No. 61/024,527, filed on Jan. 29, 2008.

(51) Int. Cl.
*A61B 17/32* (2006.01)

(52) U.S. Cl.
USPC .......................................................... 606/167

(58) Field of Classification Search
USPC .......... 606/106, 129, 167–180, 108; 600/115, 600/118, 119; 607/115–119, 126
See application file for complete search history.

(56) References Cited

U.S. PATENT DOCUMENTS

| | | | | |
|---|---|---|---|---|
| 4,576,162 A | * | 3/1986 | McCorkle | 606/159 |
| 4,651,752 A | * | 3/1987 | Fuerst | 600/567 |
| 4,886,065 A | * | 12/1989 | Collins, Jr. | 600/377 |
| 5,170,787 A | * | 12/1992 | Lindegren | 600/373 |
| 5,246,014 A | * | 9/1993 | Williams et al. | 607/122 |
| 5,456,662 A | * | 10/1995 | Edwards et al. | 604/22 |
| 5,470,308 A | * | 11/1995 | Edwards et al. | 604/22 |
| 5,651,781 A | * | 7/1997 | Grace | 606/1 |
| 6,098,629 A | | 8/2000 | Johnson et al. | |
| 6,132,456 A | * | 10/2000 | Sommer et al. | 607/127 |
| 6,185,464 B1 | * | 2/2001 | Bonner et al. | 607/119 |
| 6,338,345 B1 | | 1/2002 | Johnson et al. | |
| 6,401,718 B1 | | 6/2002 | Johnson et al. | |
| 6,605,094 B1 | * | 8/2003 | Mann et al. | 606/129 |
| 6,725,866 B2 | | 4/2004 | Johnson et al. | |
| 7,185,657 B1 | | 3/2007 | Johnson et al. | |
| 7,585,302 B2 | * | 9/2009 | Revie et al. | 606/129 |
| 7,857,819 B2 | * | 12/2010 | Jaax et al. | 606/129 |
| 2002/0148475 A1 | | 10/2002 | Johnson et al. | |
| 2005/0267555 A1 | | 12/2005 | Marnfeldt et al. | |
| 2006/0190009 A1 | * | 8/2006 | Revie et al. | 606/129 |
| 2006/0235431 A1 | * | 10/2006 | Goode et al. | 606/108 |
| 2006/0247768 A1 | | 11/2006 | Starkebaum | |
| 2007/0244490 A1 | * | 10/2007 | Moehle et al. | 606/108 |

FOREIGN PATENT DOCUMENTS

| | | |
|---|---|---|
| WO | WO-99/53994 A1 | 10/1999 |
| WO | WO-00/59398 A1 | 10/2000 |
| WO | WO-02/35986 A2 | 5/2002 |
| WO | WO-2005/118057 A2 | 12/2005 |

\* cited by examiner

*Primary Examiner* — Ryan Severson
*Assistant Examiner* — Jonathan W Miles
(74) *Attorney, Agent, or Firm* — Frommer Lawrence & Haug LLP; Bruce E. Black (57) ABSTRACT

Systems and techniques for explanting implantable devices are described. In one aspect, a device includes an explant tool configured to explant an implantable device from a body. The explant tool includes an elongate shank comprising a forward portion defining a longitudinal passage and a front tip attached to the forward portion and defining an opening to the longitudinal passage defined by the forward portion. The front tip comprises a slanted surface that slopes in a direction so as to spread tissue during forward penetration of the front tip into the body.

6 Claims, 12 Drawing Sheets

EXPLANTING IMPLANTABLE DEVICES

CROSS-REFERENCE TO RELATED APPLICATIONS

The present application claims the benefit of U.S. Provisional Patent Application No. 61/024,527 filed Jan. 29, 2008, which is incorporated herein by reference in its entirety.

BACKGROUND

This disclosure relates to explanting implantable devices.

Devices that are implanted in a body can perform any of a number of different activities, including diagnostic, therapeutic, monitoring, and other activities. At times, it may be desirable to explant (i.e., remove) an implanted device from the body. For example, the lifespan of an implanted device may have come to an end, a medical condition may have been cured, and/or alternative approaches to performing the activities of an implanted device may have been developed.

SUMMARY

Systems and techniques for explanting implantable devices are described. In one aspect, a device includes an explant tool configured to explant an implantable device from a body. The explant tool includes an elongate shank comprising a forward portion defining a longitudinal passage and a front tip attached to the forward portion and defining an opening to the longitudinal passage defined by the forward portion. The front tip comprises a slanted surface that slopes in a direction so as to spread tissue during forward penetration of the front tip into the body.

This and other aspects can include one or more of the following features. The elongate shank can include a rear portion that is more flexible than the forward portion. The device can also include a positioning member dimensioned to slide along at least a portion of the elongate shank. The elongate shank can include a longitudinal cutout positioned to open the longitudinal passage. The positioning member can include a tooth dimensioned to fill at least a portion of the longitudinal cutout.

The front tip further can include a cutting element arranged to cut through a tissue upon forward penetration of the front tip into the body. The front tip can also include a recess to hold the cutting element. The front tip can also include a cutting, a serrated, or an abrasive element arranged to cut through a tissue upon rotation of the front tip.

In another aspect, a method includes locating a flexible tail of an implantable device that is implanted in a body, inserting the flexible tail into a forward tip of an elongate explant tool, advancing the forward tip into the body, following the flexible tail; and withdrawing the implantable device from the body.

This and other aspects can include one or more of the following features. The implantable device can be art implantable pulse generator. The method can include maintaining a tension on the flexible tail while advancing the forward tip into the body, e.g., by pulling on a terminal portion of the flexible tail from outside the body. The flexible tail can be inserted into the forward tip by threading the flexible tail through a passage through the forward tip. The forward tip can be advanced by reaching a device body of the implantable device with the forward tip. The method can also include cutting or serrating a tissue capsule around the device body.

The implantable device can be withdrawn from the body through a tissue passage formed by advancement of the forward tip into the body. The forward tip can include a slanted surface beside the passage. The forward tip can be advanced by spreading tissue around the tail using the slanted surface to pass the forward tip. An active element can be removed from the flexible tail of the implantable device prior to the insertion of the flexible tail into the forward tip. The forward tip can be advanced by sliding a positioning member along a shank connected to the forward tip, wherein sliding the positioning member maintains the positioning member outside the body.

In another aspect, a system includes an implantable device comprising a device body attached to a flexible tail and an explant tool comprising a tip mounted on a shank, wherein the tip defines a passage dimensioned to pass the sectional area of the flexible tail of the implantable device. The flexible tail has a sectional area over at least a portion of its length.

This and other aspects can include one or more of the following features. The implantable device can include a first dimension lateral to a site at which the device body is attached to the tail. The shank can include a second dimension in a vicinity of the tip. The second dimension can be lateral to the shank. The second dimension can be the same size or larger than the first dimension.

The implantable device can include an implantable pulse generator. The flexible tail can include an active element configured to participate in a performance of activities by the implantable device. The implantable device can also include a positioning member dimensioned to slide along at least a portion of the shank. The shank can also define the passage defined by the tip. The positioning member can be configured to maintain a portion of the flexible tail in a portion of the passage defined by the shank.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
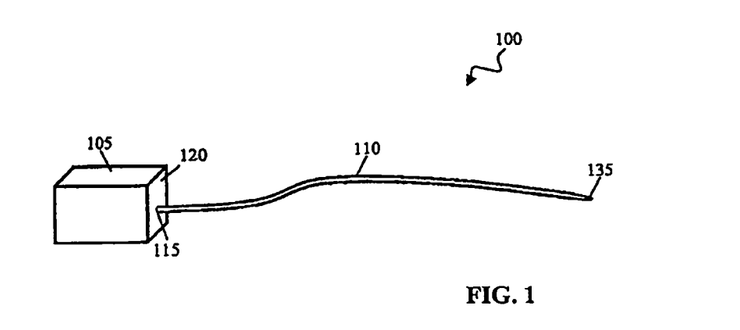
FIGS. 1 and 2 are schematic representations of implantable devices that may have occasion to be explanted.
Figure 2:
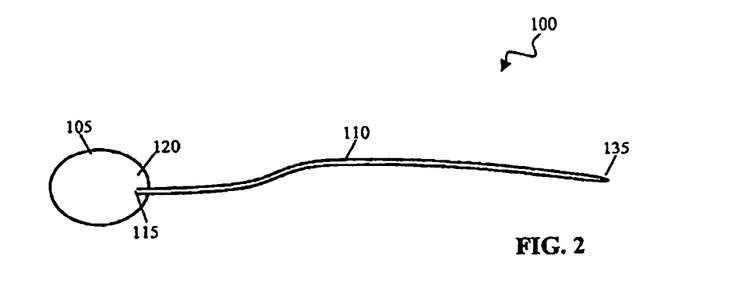

FIGS. 1 and 2 are schematic representations of implantable devices 100 that may have occasion to be explanted. Each implantable device 100 includes a device body 105 and a tail 110. Each device body 105 includes a biocompatible housing that houses elements configured to perform activities when the corresponding implantable device 100 is implanted in a body. For example, each device body 105 can include mechanical, electrical, chemical, biological, and/or optical components that perform, e.g., diagnostic, therapeutic, monitoring, and/or other activities after implantation.

In some implementations, implantable devices 100 are implantable pulse generators. An implantable pulse generator (IPG) is an implantable device that delivers electrical pulses to cells or tissue. The electrical pulses can be delivered for therapeutic, functional, diagnostic, or other purposes. When implantable device 100 is an implantable pulse generator, the elements housed in device body 105 can include, e.g., one or more power storage devices such as a battery, one or more electrodes for delivery of the electrical pulses, and/or control circuitry for managing the delivery of the electrical pulses.

Tails 110 are generally flexible, elongate members that are each attached to a corresponding device body 105 at an attachment site 115. Each attachment site 115 is found on a surface 120 of device body 105 of a corresponding implantable device 100. Surface 120 extends laterally outward from attachment site 115. Tails 110 are thus thinner than device bodies 105 in that at least a portion of device bodies 105 have a larger cross-section than tails 110. In some implementations, the cross-sections of tails 110 are generally uniform along their entire length. In other implementations, the cross-sections of tails 110 are not uniform along their entire length but may include elements that can be detached or otherwise removed to achieve a uniform cross-section. Each tail 110 extends longitudinally from attachment site 115 to an end 135.

Tails 110 can be formed from one or more flexible polymeric, ceramic, or metallic biocompatible materials, such as nylon, polytetrafluoroethylene, silicone, polyurethane, polyester, polypropylene, titanium, carbon fiber, stainless steel, noble metals, glass fibers, and the like. In some implementations, tails 110 can be formed from bioresorbable materials if the expected duration of implantation is shorter than the time for resorbtion. The material forming tails 110 can be shaped into wires or other elongate strands. In some implementations, the wires or strands can be woven or threaded to form a stranded tails 110. In other implementations, tails 110 can be solid.

Tails 110 can be completely passive or can include one or more active components. Active tails 110 can include one or more mechanical, electrical, chemical, biological, and/or optical components that contribute to the performance of activities by implantable device 100. For example, active tails 110 can include active components such as optical fibers, fluid conduits, and/or electrical leads that are covered by one or more electrical insulators.

In operation, device bodies 105 of implantable devices 100 can be implanted at relatively "deep" sites, while tails 110 can extend to relatively superficial sites closer to the skin or other surface. This arrangement can have a number of different advantages. For example, a tail 110 can guide medical personnel from a superficial site to a device body 105 of an implanted device 100 that it implanted at a deeper site with minimal collateral tissue damage, as discussed further below. As another example, if an active tail 110 includes a charging element that contributes to the conversion of energy from outside a body into potential energy, the charging element can be positioned close to the skin surface so that a relatively small amount of the energy from outside the body is dissipated by transmission through the body.

Figure 3:
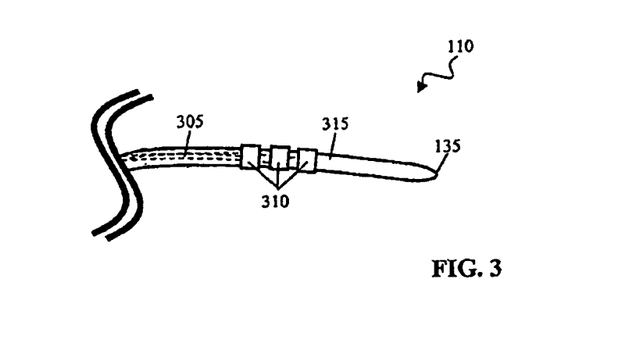
FIGS. 3 and 4 are schematic representations of tails of implantable devices that include active components.

FIG. 3 is a schematic representation of a tail 110 that includes active components, namely, one or more leads 305 and one or more electrodes 310. Leads 305 are wires that place electrodes 310 in electrical contact with components in device body 105 of an implantable device 100. The conducting path formed by leads 305 and electrodes 310 traverses an outer surface 315 of tail 110 so that electrodes 310 can deliver electrical pulses originating in device body 105 to sites that are relatively remote from device body 105.

Figure 4:
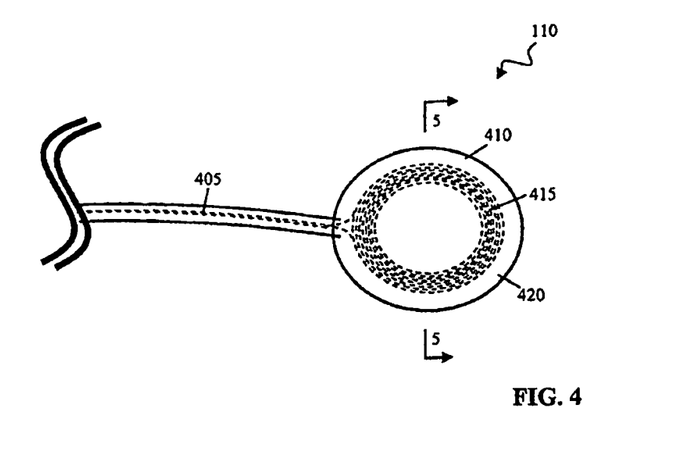
Figure 5:
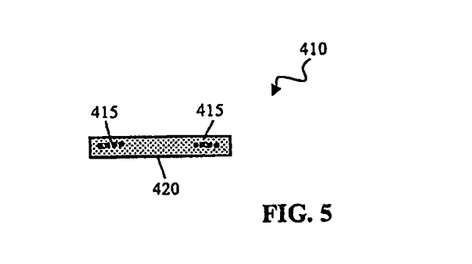
FIG. 5 is a sectional representation of the active component of the tail of FIG. 4.

FIG. 4 is a schematic representation of a tail 110 that includes active components, namely, a pair of leads 405 and a charging element 410. FIG. 5 is a sectional representation of charging element 410 along the line 5-5 of FIG. 4.

Charging element 410 includes a coiled conductor 415 that is housed in a biocompatible casing 420. Leads 405 are wires that place coiled conductor 415 in electrical contact with components in device body 105 of implantable device 100. Coiled conductor 415 can respond to a magnetic or electric field generated outside the body in which implantable device 100 is implanted. The motion of electrons in coiled conductor 415 under the influence of such a magnetic or electric field can be converted into potential energy and stored, e.g., at a rechargeable battery or other energy storage device in device body 105 of implantable device 100.

The conducting path formed by leads 405 to coiled conductor 415 allows charging element 410 to be positioned close to the skin surface while device body 105 is implanted at a deeper site. Such a positioning can reduce the dissipation of the magnetic or electric field from outside the body while allowing the motion induced by such a field in coiled conductor 415 to be efficiently conveyed to device body 105.

Figure 6:
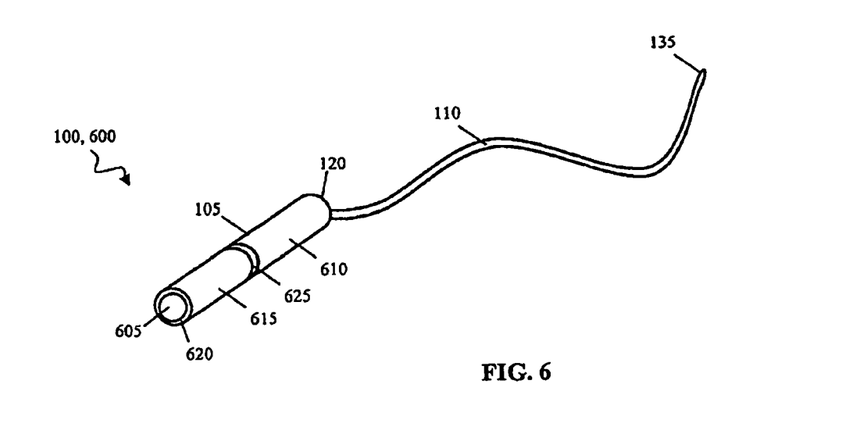
FIG. 6 is a schematic representation of one example of an implantable device that may have occasion to be explanted.

FIG. 6 is a schematic representation of one example of an implantable device 100, namely, an implantable microstimulator 600. Implantable pulse generator 600 includes a generally cylindrical device body 105 and tail 110 that is attached to a surface 120 which caps device body 105. Device body 105 can be dimensioned to be implantable through the cannula of a closed surgical device. Device body 105 houses electrical circuitry, power storage devices, and other components for the delivery of electrical stimuli to cells or tissue.

Implantable pulse generator 600 also includes a stimulating electrode 605 and a counter electrode 610 that are separated by an insulator 615. Stimulating electrode 605 is positioned on a cap 620 of device body 105. Counter electrode 610 and insulator 615 are generally cylindrical members with the same circumferential outer surface geometry. Counter electrode 610 and insulator 615 are joined at a seam 625 with their outer surfaces aligned.

Figure 7:
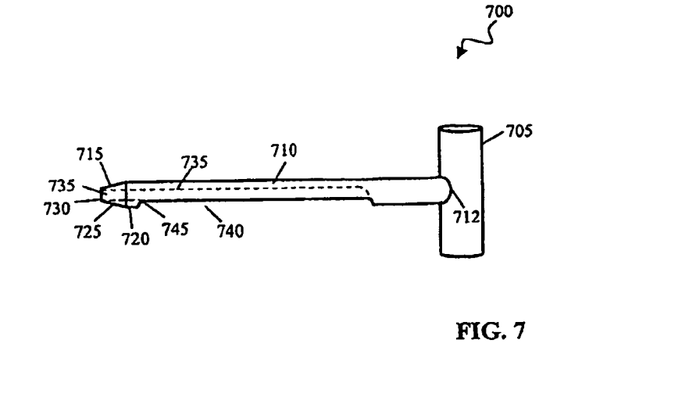
FIG. 7 is a schematic representation of an explant tool.
Figure 8:
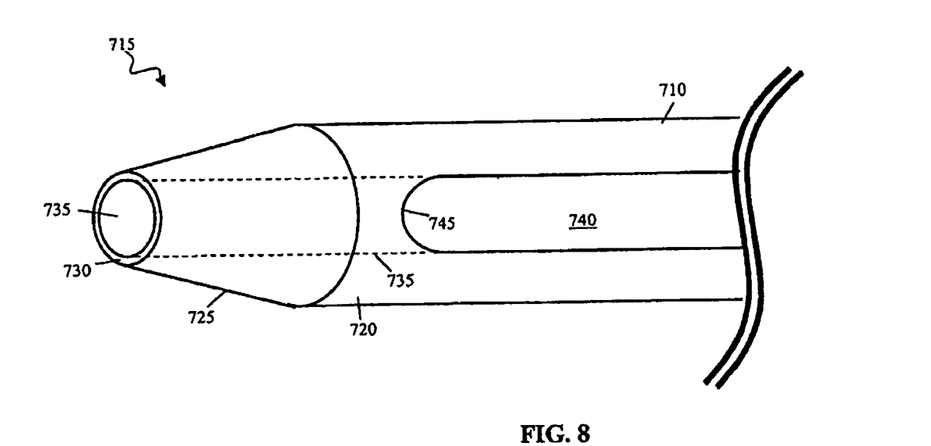
FIGS. 8-10 are schematic representations of implementations of tips of the explant tool of FIG. 7.

FIG. 7 is a schematic representation of an explant tool 700. Explant tool 700 includes a handle 705 that is fixed to an elongate shank 710 at a site 712. Shank 710 extends longitudinally away from handle 705 to terminate in a tip 715. Tip 715 can have a truncated conical shape (as shown), a blunted, bullet shape, a truncated pyramidal shape, or other shape that includes one or more slanted surfaces that slope to spread tissue during forward penetration of tip 715 into the body. FIG. 8 is a schematic representation of the truncated conical implementation of tip 715 in additional detail. In the vicinity of tip 715, shank 710 includes an outer circumference 720. The truncated cone of tip 715 includes a slanted surface 725 that slopes inward from outer circumference 720 to an end 730 of tip 715. Outer circumference 720 can be dimensioned to be the same size or larger than a lateral size an implantable device that is to be explanted, as discussed further below.

Tip 715 and at least a portion of shank 710 define a passage 735. Passage 735 extends longitudinally into the truncated cone of tip 715 and through the forward portion of shank 710.

Shank 710 includes a cutout 740 that communicates with end 730 via passage 735. Cutout 740 ends the generally circular outer diameter 720 of shank 710 in a rounded edge 745. Passage 735 can be dimensioned to receive the tail of an implantable device that is to be explanted, as discussed further below.

In some implementations, end 730 of tip 715 can include one or more elements to aid in the penetration of tip 715 into a body. For example, end 730 can include a blade or other sharpened edge for cutting through tissue. As another example, end 730 can be serrated or include abrasive elements for sawing through tissue upon rotation.

Figure 9:
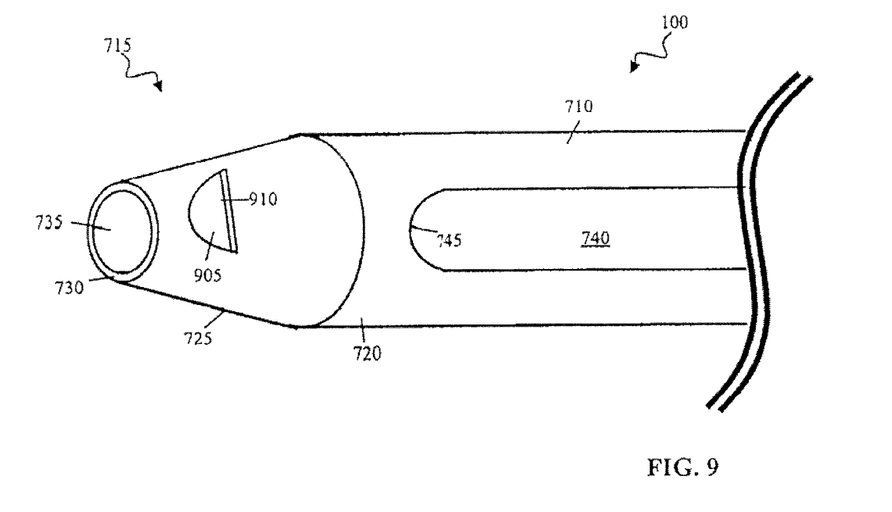

FIG. 9 is a schematic representation of another implementation of tip 715. In the illustrated implementation, slanted surface 725 defines one or more lateral depressions 905. A blade 910 or other cutting element is recessed in each depression 905. Blade 910 is oriented laterally relative to shank 710 and can cut tissue that moves into depression 905 during the forward penetration of tip 715 into a body.

Figure 10:
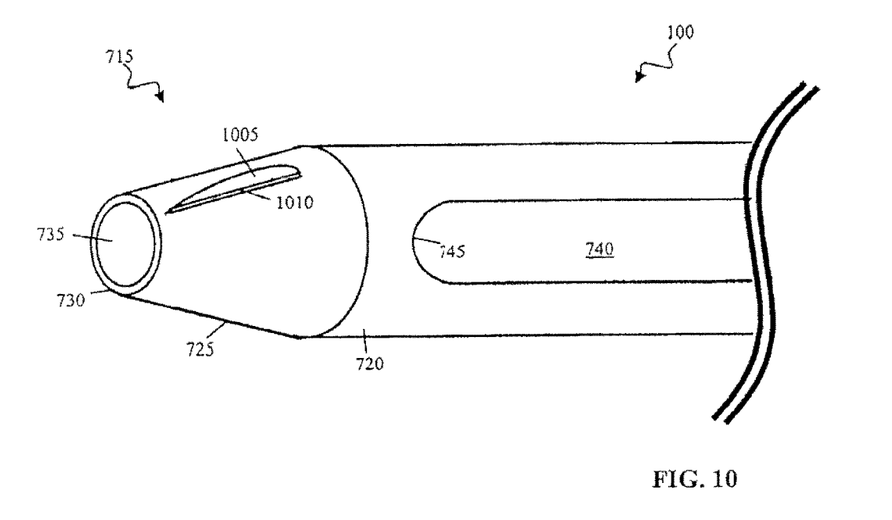

FIG. 10 is a schematic representation of another implementation of tip 715. In the illustrated implementation, slanted surface 725 defines one or more longitudinal depressions 1005. A blade 1010 or other cutting element is recessed in each depression 1005. Blade 1010 is oriented longitudinally along shank 710 and can cut tissue that moves into depression 905 upon rotation of tip 715 during the penetration of a body.

Figure 11:
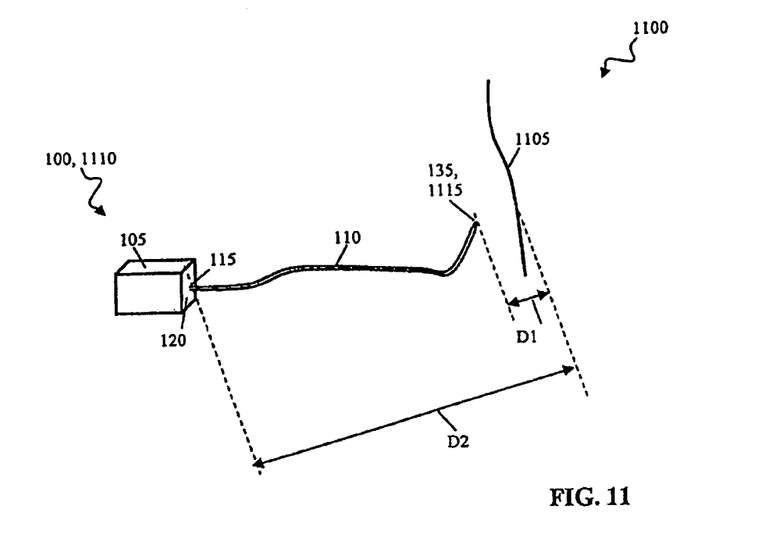
FIGS. 11-17 schematically represent an illustrative example of the use of the explant tool of FIG. 7 to explant an implantable device from a body.

FIGS. 11-17 schematically represent an illustrative example of the use of explant tool 700 to explant an implantable device 100 from a body 1100. With reference to FIG. 11, body 1100 includes a body surface 1105 by which medical personnel can access implantable device 100. Body surface 1105 is generally the skin.

Implantable device 100 is implanted in body 1100 with device body 105 positioned at a relatively deep site 1110 and with tail 110 extending to a superficial site 1115 closer to surface 1105. Thus, superficial site 1115 is at a depth D1 beneath surface 1105 and surface 120 of device body 105 is at a depth D2 beneath surface 1105. Depth D1 is smaller than depth D2.

Figure 12:
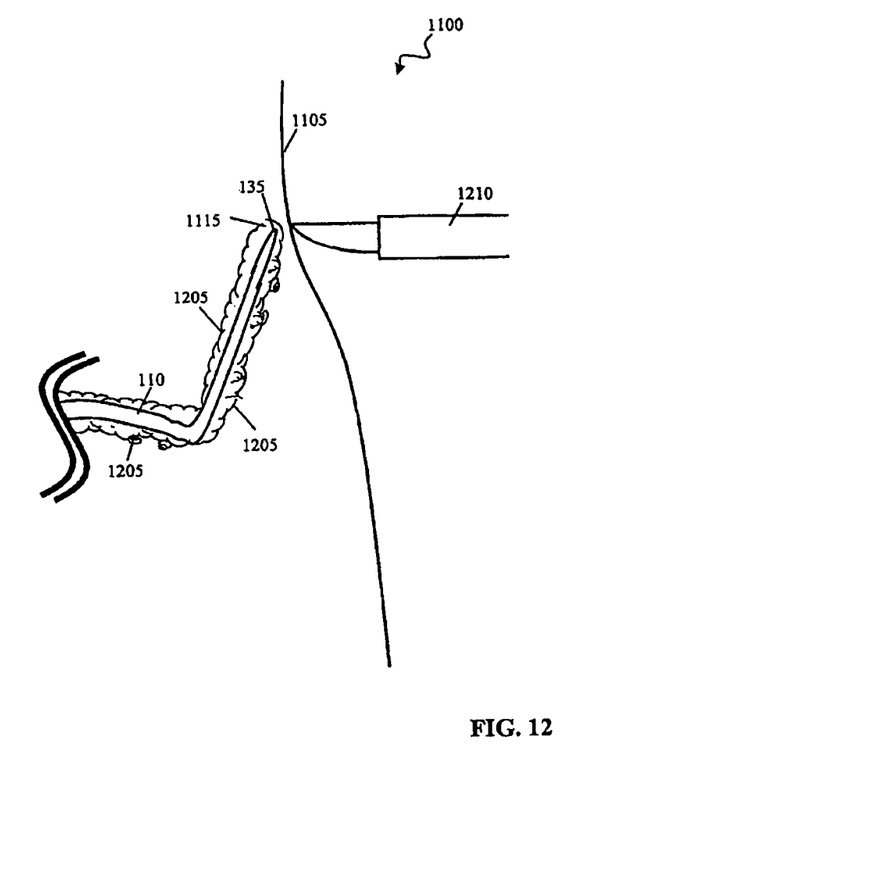
Figure 13:
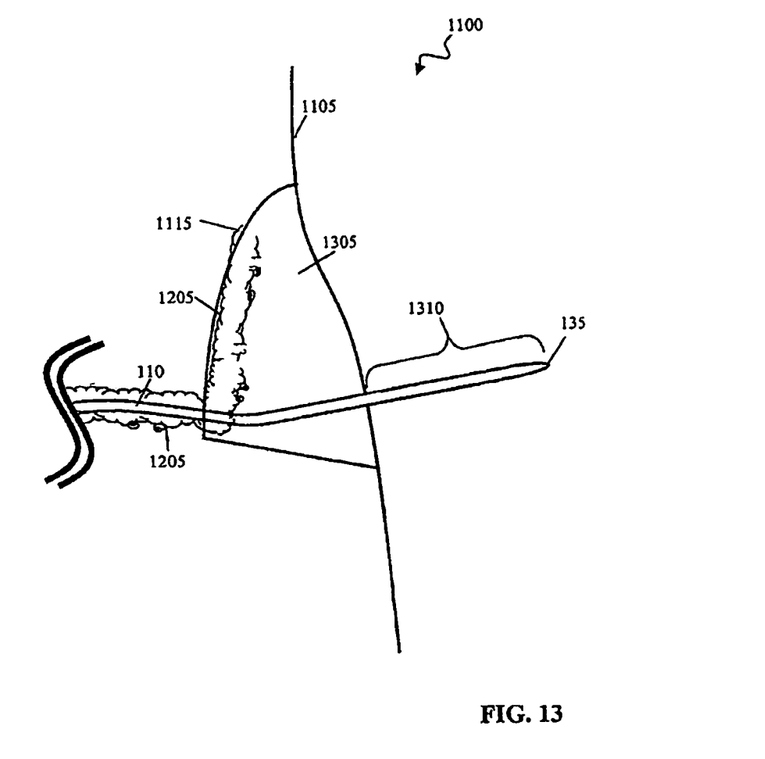

With reference to FIGS. 12-13, after a sufficiently long implantation term, implantable device 100 will often become encased in a tissue capsule 1205. Medical personnel can make an incision 1305 in the vicinity of end 135 of tail 110 using a scalpel 1210 or other device. The exposed portion of tissue capsule 1205 can also be cut and the terminal portion 1310 of tail 110 can be teased out from body 1100. Since superficial site 1115 is at a depth D1 beneath body surface 1105, incision 1305 is relatively shallow despite the implantation of device body 105 of device 100 at a deeper location.

In implementations where tail 110 includes one or more active components, such as charging element 410, that are relatively large, the active components can be detached or otherwise removed from the remainder of tail 110. For example, tail 110 can be cut to remove charging element 410.

Figure 14:
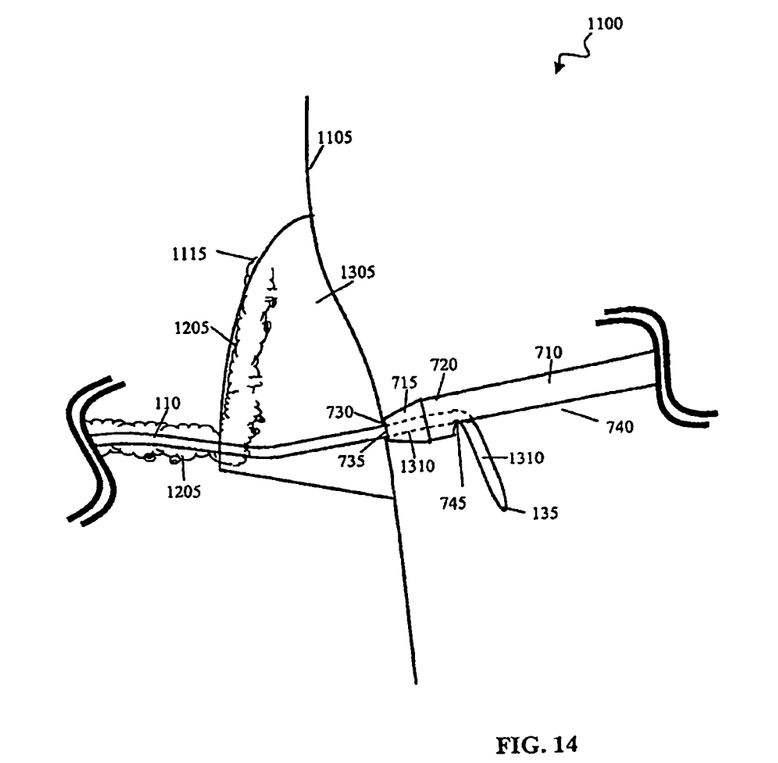
Figure 15:
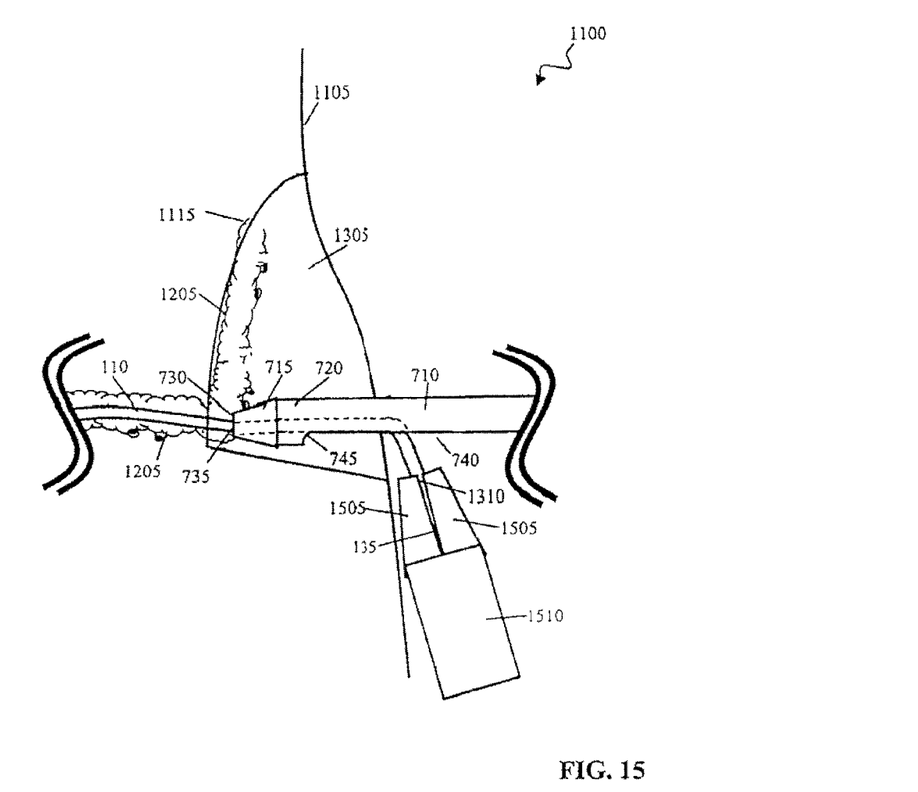

With reference to FIGS. 14 and 15, the terminal portion 1310 of tail 110 can be inserted into end 710 of explant tool 700 by threading tail 110 through passage 735 and out into cutout 740. The terminal portion 1310 of tail 110 can then be grasped between the jaws 1505 of hemostat or other pliers 1510. Explant tool 700 can be advanced into incision 1305 by medical personnel manipulating handle 705 (not shown). Pliers 1510 can maintain tension on tail 110 while explant tool 700 is advanced.

Figure 16:
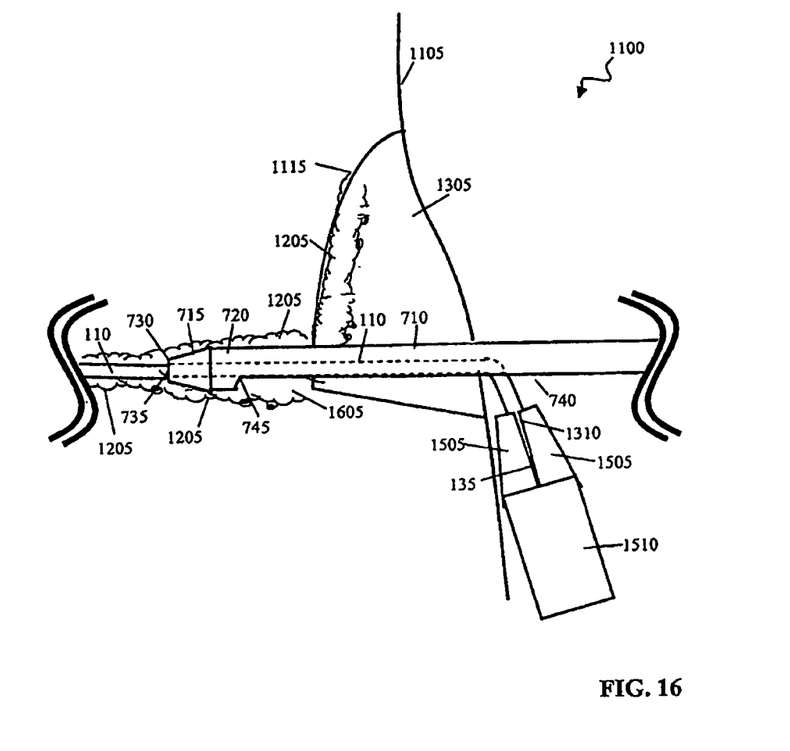

With reference to FIGS. 15 and 16, while maintaining grip on terminal portion 1310 of tail 110, further manipulation can be used to advance tip 715 along tail 110 and deeper into body 1100 toward device body 105 of implantable device 100. If necessary, explant tool 700 can be pushed or rotated using handle 705 to aid in the penetration of tip 715 through tissue capsule 1205 that surrounds tail 110. Such manipulation can bring blades, serrated edges, and/or abrasive elements to bear on tissue capsule 1205. As tip 715 penetrates into body 1100 along tail 110, slanted surface 725 spreads tissue capsule 1205 to create a channel 1605. Channel 1605 can thus pass solid objects with diameters that are the same size or smaller than outer circumference 720 of shank 710.

Figure 17:
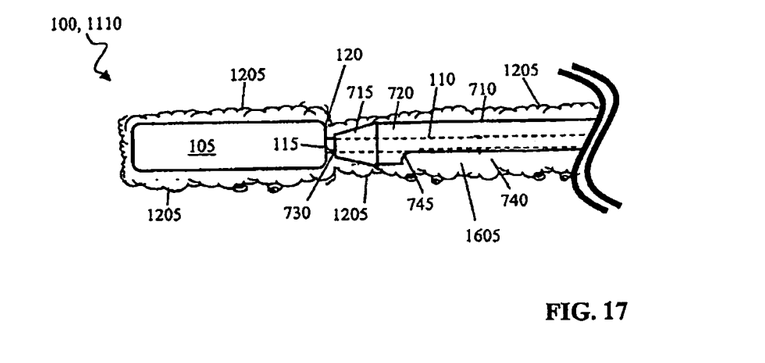

With reference to FIG. 17, following tail 110, tip 715 of explant tool 700 can reach site 1110 where device body 105 of implantable device 100 is implanted. If necessary, tip 715 of explant tool 700 can be used to penetrate any tissue capsule 1205 around surface 120 of device body 105 to clear the way for withdrawal of device body 105 through channel 1605. Implantable device 100 can be explanted through channel 1605 by pulling explant tool 700, along with the gripped terminal portion 1310 of tail 110, away from body 1100.

Figure 18:
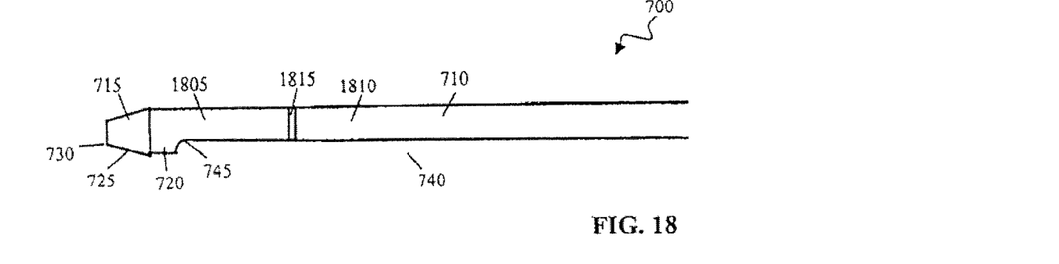
FIG. 18 is a schematic representation of another implementation of an explant tool.

FIG. 18 is a schematic representation of another implementation of explant tool 700. In the illustrated implementation, shank 710 of explant tool 700 includes a relatively flexible portion 1810 and a relatively inflexible portion 1805 that is joined to tip 715. Relatively inflexible portion 1805 is less flexible than relatively flexible portion 1810 and hence better suited for penetrating into a body. In particular, a relatively less flexible and harder dissection tip can facilitate penetration of the tissue and decrease deformation of the dissection tip.

The different flexibilities of relatively inflexible portion 1805 and relatively flexible portion 1810 can be achieved in a number of different ways. For example, portion 1805 can be made from a first, relatively inflexible, polymer and portion 1810 can be made from a second, relatively flexible, polymer. As another example, portion 1805 and portion 1810 can have identical compositions but different structures. For example, passage 735 can be larger in portion 1810 than in portion 1805. As yet another example, the materials used to form portions 1805, 1810 can be handled in different ways and/or include different compositions.

In some implementations, portions 1805, 1810 are joined at a seam 1815. In other implementations, shank 710 can be formed as a unitary structure and portions 1805, 1810 can be separated by a gradient or other transition in flexibility.

Figure 19:
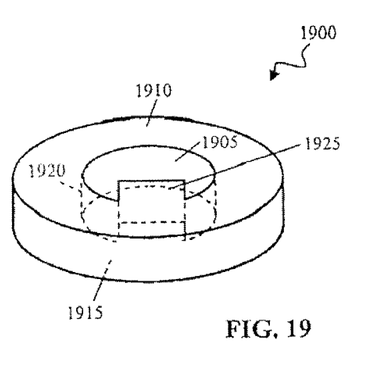
FIG. 19 is a diagrammatic view of a positioning member.
Figure 20:
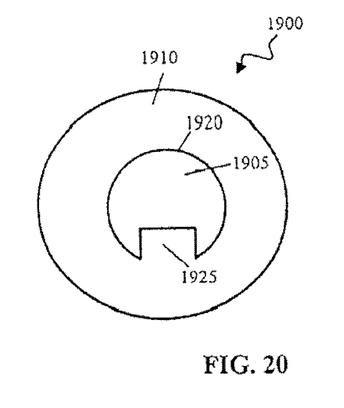
FIG. 20 is a view of the positioning member of FIG. 19 from above.

FIG. 19 is a diagrammatic view of a positioning member 1900. FIG. 20 is a view of positioning member 1900 from above. Positioning member 1900 is a generally planar member that includes an interior wall 1920. Interior wall 1920 extends from a first face 1910 to a second face 1915 of positioning member 1900 to define a passage 1905 therethrough. Interior wall 1920 also defines a lateral tooth 1925 that extends toward the interior of passage 1905.

Figure 21:
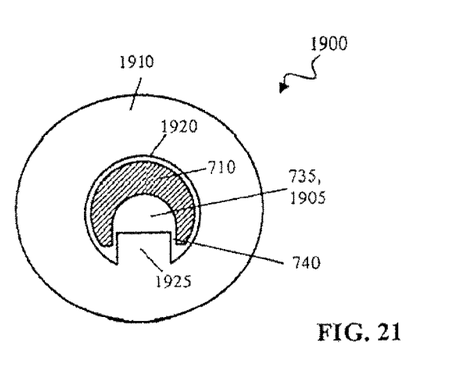
FIG. 21 is a schematic representation of the reception of a portion of an explant tool in the positioning member of FIG. 19.

Positioning member 1900 is dimensioned to slidably receive the portion of shank 710 that includes cutout 740. FIG. 21 is a schematic representation of the reception of this portion of shank 710 in positioning member 1900. As shown, cutout 1905 is dimensioned to pass this portion of shank 710 with lateral tooth 1925 extending into cutout 740. In extending into cutout 740, lateral tooth 1925 can prevent the entry of a tail 110 into cutout 740. Lateral tooth 1925 does not however, extend into passage 735. Rather, passage 735 can pass a tail 110 of an implantable device 100. The Portion of shank 710 that includes cutout 740 can be slid forward and backward (i.e., in and out of the page) through positioning member 1900.

Figure 22:
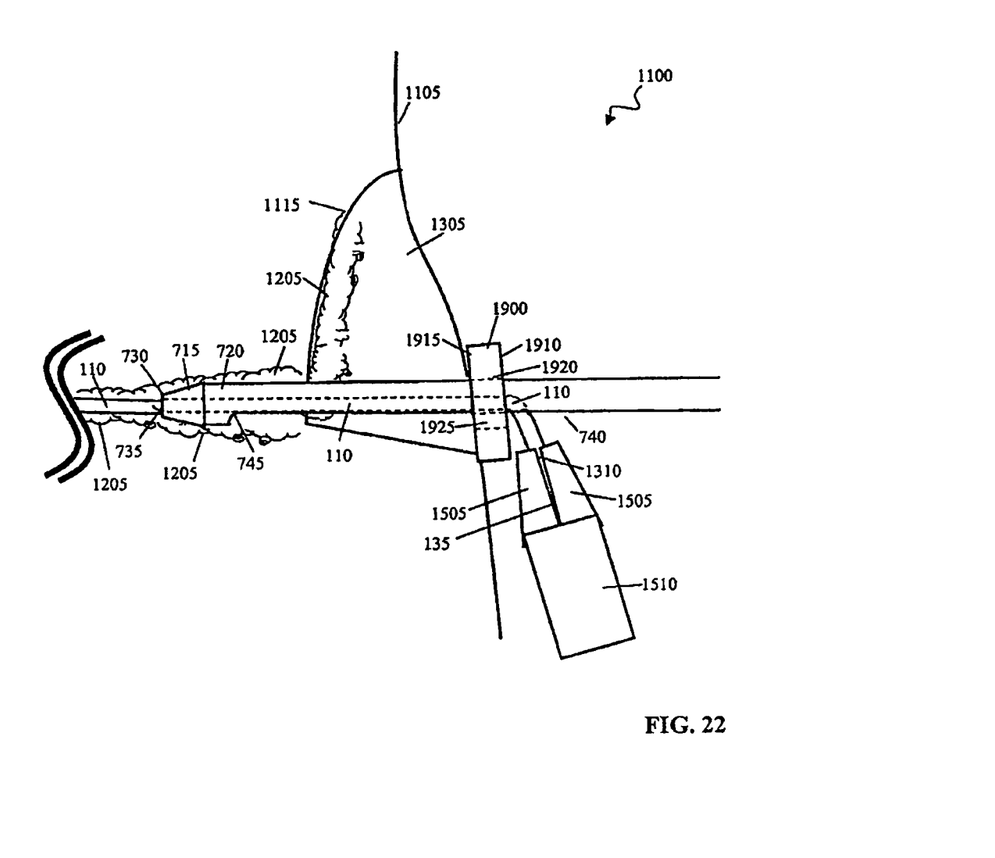
FIG. 22 schematically represents the use of a positioning member and an explant tool to explant an implantable device from a body.

FIG. 22 schematically represents the use of positioning member 1900 and explant tool 700 to explant an implantable device 100 from a body 1100. As shown, the portion of shank

710 that includes cutout 740 is received in positioning member 1900. Positioning member 1900 is maintained outside of body 1100 and can rest against body surface 1105. Tail 110 is threaded into tip 715 and follows passage 735 past positioning member 1900 and out of body 1100. Positioning member 1900 thus prevents the entry of tail 110 into cutout 740 before tail 110 exits body 1100.

A number of implementations have been described. Nevertheless, it will be understood that various modifications may be made. For example, other charging elements, including optical (e.g., photovoltaic cells) and mechanical (e.g., piezoelectric devices) elements, can be used. As another example, a tail 110 need not be teased out from the body before insertion into passage 735 of an explant tool 700. As yet another example, a positioning member 1900 need not include a tooth 1925. Accordingly, other implementations are within the scope of the following claims.

What is claimed is:

1. A system comprising:
   an implantable device comprising a device body attached to a flexible tail, wherein the flexible tail has a sectional area over at least a portion of its length; and
   an explant tool comprising a shank and a tip mounted on the shank, wherein the tip and the shank define a longitudinal passage dimensioned to pass the sectional area of the flexible tail of the implantable device and the shank further defines a first end and a longitudinal cutout positioned to open the longitudinal passage and, wherein a portion of the implantable device extends through the longitudinal passage and out of the shank through the longitudinal cutout, wherein the tip is mounted on the first end of the shank and the longitudinal cutout is spaced apart from the first end of the shank so that the longitudinal cutout terminates before the first end of the shank and before the tip.

2. The system of claim 1, wherein:
   the implantable device comprises a first dimension lateral to a site at which the device body is attached to the tail;
   the shank comprises a second dimension in a vicinity of the tip, wherein the second dimension is lateral to the shank; and the
   second dimension is the same size or larger than the first dimension.

3. The system of claim 1, wherein the implantable device comprises an implantable pulse generator.

4. The system of claim 1, wherein the flexible tail comprises an active element configured to participate in a performance of activities by the implantable device.

5. The system of claim 1, wherein the system further comprises a positioning member disposed circumferentially around a portion of the shank and dimensioned to slide along at least a portion of the shank.

6. The system of claim 5, wherein
   the positioning member is configured to maintain a portion of the flexible tail in a portion of the longitudinal passage defined by the shank.

\* \* \* \* \*